(12) United States Patent
Nozato et al.

(10) Patent No.: US 9,254,083 B2
(45) Date of Patent: Feb. 9, 2016

(54) LIGHT SOURCE MODULATION FOR A SCANNING MICROSCOPE

(71) Applicants: CANON KABUSHIKI KAISHA, Tokyo (JP); University of Rochester, Rochester, NY (US)

(72) Inventors: Koji Nozato, Rochester, NY (US); Qiang Yang, Rochester, NY (US)

(73) Assignees: Canon Kabushiki Kaisha, Tokyo (JP); UNIVERSITY OF ROCHESTER, Rochester, NY (US)

(*) Notice: Subject to any disclaimer, the term of this patent is extended or adjusted under 35 U.S.C. 154(b) by 7 days.

(21) Appl. No.: 14/099,700

(22) Filed: Dec. 6, 2013

(65) Prior Publication Data

US 2015/0157204 A1 Jun. 11, 2015

(51) Int. Cl.
*A61B 3/14* (2006.01)
*A61B 3/12* (2006.01)
*A61B 3/13* (2006.01)

(52) U.S. Cl.
CPC .... *A61B 3/12* (2013.01); *A61B 3/13* (2013.01)

(58) Field of Classification Search
CPC ............... A61F 9/008; A61F 9/0079; A61F 2009/00897; G02B 26/127; G02B 21/002; G02B 21/0024; A61B 1/00172; A61B 2018/2085
USPC ............... 348/79; 351/206; 359/201.2–203.1, 359/205.1
See application file for complete search history.

(56) References Cited

U.S. PATENT DOCUMENTS

| | | | |
|---|---|---|---|
| 2010/0027020 A1* | 2/2010 | Nebosis | 356/450 |
| 2010/0165291 A1 | 7/2010 | Sugita et al. | |
| 2011/0221739 A1* | 9/2011 | Masui | 345/213 |
| 2012/0296319 A1 | 11/2012 | Chaudhary et al. | |
| 2013/0050156 A1 | 2/2013 | Rothaar | |

FOREIGN PATENT DOCUMENTS

| | | |
|---|---|---|
| JP | 1989032700 B2 | 7/1989 |
| JP | 2005-315574 A | 11/2005 |
| JP | 2005315574 A | 11/2005 |

OTHER PUBLICATIONS

Hakan Urey, Ned Nestorovic, Baldwin Ng, Abraham Gross, Optics Designs and System MTF for Laser Scanning Displays, Aerosense'99, Helmet and Head-Mounted Displays IV, Orlando, Apr. 5, 1999, SPIE Proceedings, Jul. 12, 1999, vol. 3689, SPIE, Bellingham, WA, 1999.

(Continued)

*Primary Examiner* — Mahidere Sahle
(74) *Attorney, Agent, or Firm* — Canon USA, Inc. I. P. Division

(57) ABSTRACT

Systems, method, and non-transitory computer readable medium for imaging an object. The system includes a scanner. The scanner positions a spot of light from a light source on the object along a scanning path. The scanning path includes a plurality of scan lines. The spot moves along the scanning path at a scanning velocity. The scanning velocity is not constant. The intensity of the spot of light is modulated as a function of the scanning velocity. The system includes a detector that is arranged to output data associated with positions along the scanning path. The system includes one or more processors that perform calculations. Pixels are calculated based on the output data. The image is constructed of the object based on the pixels.

13 Claims, 7 Drawing Sheets

(56) References Cited

OTHER PUBLICATIONS

Qiang Yang, David W. Arathorn, Pavan Tiruveedhula, Curtis R. Vogel, Austin Roorda, Design of an Integrated Hardware Interface for AOSLO Image Capture and Cone-Targeted Stimulus Delivery, Optics Express, Aug. 16, 2010, 18(17):17841-17858, Optical Society of America, Washington DC, 2010.

* cited by examiner

LIGHT SOURCE MODULATION FOR A SCANNING MICROSCOPE

GOVERNMENT LICENSE RIGHTS

This invention was made with government support under grant numbers EY014375 and EY001319 awarded by the National Institutes of Health. The Government has certain rights in the invention.

BACKGROUND

1. Field of Art

The present disclosure relates to a scanning imaging system, methods, and non-transitory computer readable medium with instructions for modulating a light source.

2. Description of the Related Art

Laser confocal microscopes and Scanning Laser Ophthalmoscopes (SLO), obtain a two dimensional images of a specimen by employing two scanners to dynamically update positions of a laser spot on the specimen. The two scanners are a resonant scanner and a linear scanner. The resonant scanner, also called the "fast scanner" oscillates back and forth at kHz rates to update the position of the laser spot in a first direction (e.g., X direction in Cartesian coordinates). The linear scanner, also called the "slow scanner" oscillates back and forth at Hz rates to update the position of the laser spot in a second direction perpendicular to the first direction (e.g., Y direction in Cartesian coordinates). The two scanners work together to sweep the laser spot across a portion of the specimen being imaged (scanning area), producing a two dimensional image of the specimen. The fast scanner is typically driven by a sinusoidal signal (or a similar such signal) to achieve high-speed scanning hence its physical motion is also sinusoidal or very close to sinusoidal. The slow scanner is driven by a periodic ramp signal or saw-tooth signal.

One of the consequences of using a resonant scanner is that the scanning speed at the center of the scanning area is much faster than the scanning speed at the edge of the scanning area. In the prior art the intensity of the laser spot before it enters the scanner is kept constant before it enters the scanner. Thus, the radiant flux (radiant energy per unit time) is greater at the edges than at the center.

The light reflected from the specimen is detected by a photo detector such as a Photo Multiplier Tube (PMT) or an Avalanche Photo Diode (APD), and the detected signal from the detector is converted by an Analog/Digital converter (ADC) to a digital signal. The detected signal strength is proportional to the intensity of the illumination light at the specimen. When measuring the relative intensity with the detector, the detector is calibrated relative to the intensity of the illumination light received by the specimen. In order to minimize calibration error the measurement window is limited to a central area of the scanning area in which the scanning speed is substantially constant. Thus, the illumination light at the specimen in the measurement window is relatively constant. The detected signals are then truncated and reshaped according to the scanner movement in order to obtain a final image.

When the specimen is a human eye, laser safety is an important issue. Scanning Laser Ophthalmoscopes are designed to be in compliance with ANSI Z136 Laser Safety Standards, thus the radiant flux received by the eye during the measurement process is kept below a maximum intensity. If the source intensity is kept constant then the source intensity is limited to the light received at the edges of the scanning window. Alternatively, the light source is modulated so that the light source is OFF at the edges of the scanning window and is only ON during or around the measurement window.

Some scanning projectors include systems in which light passes through an optical filter that variably attenuate the light beam as function of position. These systems are inappropriate for imaging systems in which the intensity of light source should be dynamically adjustable to compensate for the dynamic variability of the imaging system.

Sometimes it is better to use non-constant source illumination so that the specimen receives uniform illumination. When the specimen receives uniform illumination than the thermal and photochemical effect of the illumination on the specimen is also uniform. The existing technologies modulate the detection laser using only two states, ON/OFF. Thus, the whole scanning area is not used for imaging because edges of the area are not illuminated.

SUMMARY

System, method, and non-transitory computer readable medium for imaging an object. The system includes a scanner. The scanner positions a spot of light from a light source on the object along a scanning path. The scanning path includes a plurality of scan lines. The spot moves along the scanning path at a scanning velocity. The scanning velocity is not constant. The intensity of the spot of light is modulated as a function of the scanning velocity. The system includes a detector that is arranged to output data associated with positions along the scanning path. The system includes one or more processors that perform calculations. Pixels are calculated based on the output data. The image of the object is constructed based on the pixels.

An aspect of at least one exemplary embodiment comprises an external modulator for modulating the light source. An aspect of at least one exemplary embodiment comprises directly modulating the light source.

An aspect of at least one exemplary embodiment comprises calculating the pixels by integrating the intensity of the detected light.

In an aspect of at least one exemplary embodiment the intensity of the spot of light is modulated as a function of the average scanning velocity.

In an aspect of at least one exemplary embodiment the average scanning velocity is averaged over a period equal to the pixel clock time.

In an aspect of at least one exemplary embodiment the intensity of the spot of light is modulated as function of the scanning velocity during a first window, and the intensity of the spot of light is substantially zero outside of the first window.

In an aspect of at least one exemplary embodiment the scanner is a resonant scanner that positions the spot of light with sinusoidal motion. Constructing the image comprises correcting image distortion caused by the sinusoidal motion by integration.

An aspect of at least one exemplary embodiment is an imaging method for imaging an object. The imaging method comprises scanning a spot of light from a light source on the object along a scanning path. The scanning path includes a plurality of scan lines. The spot moves along the scanning path at a scanning velocity. The scanning velocity is not constant. The intensity of the spot of light is modulated as a function of the scanning velocity. The output data associated with positions along the scanning path is detected. Pixels are calculated based on the output data. An image is constructed of the object based on the pixels.

An aspect of at least one exemplary embodiment is a non-transitory computer readable medium encoded with instructions for imaging an object. The instructions include sending instructions to a scanner to scan a spot of light from a light source on the object along a scanning path. The scanning path includes a plurality of scan lines. The spot moves along the scanning path at a scanning velocity. The scanning velocity is not constant. The instruction includes sending instructions to modulate the intensity of the spot of light as a function of the scanning velocity. Receiving output data from a detector. The output data is associated with positions along the scanning path. Calculating pixels based on the output data. Constructing an image of the object based on the pixels.

Further features and aspects will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Figure 1:
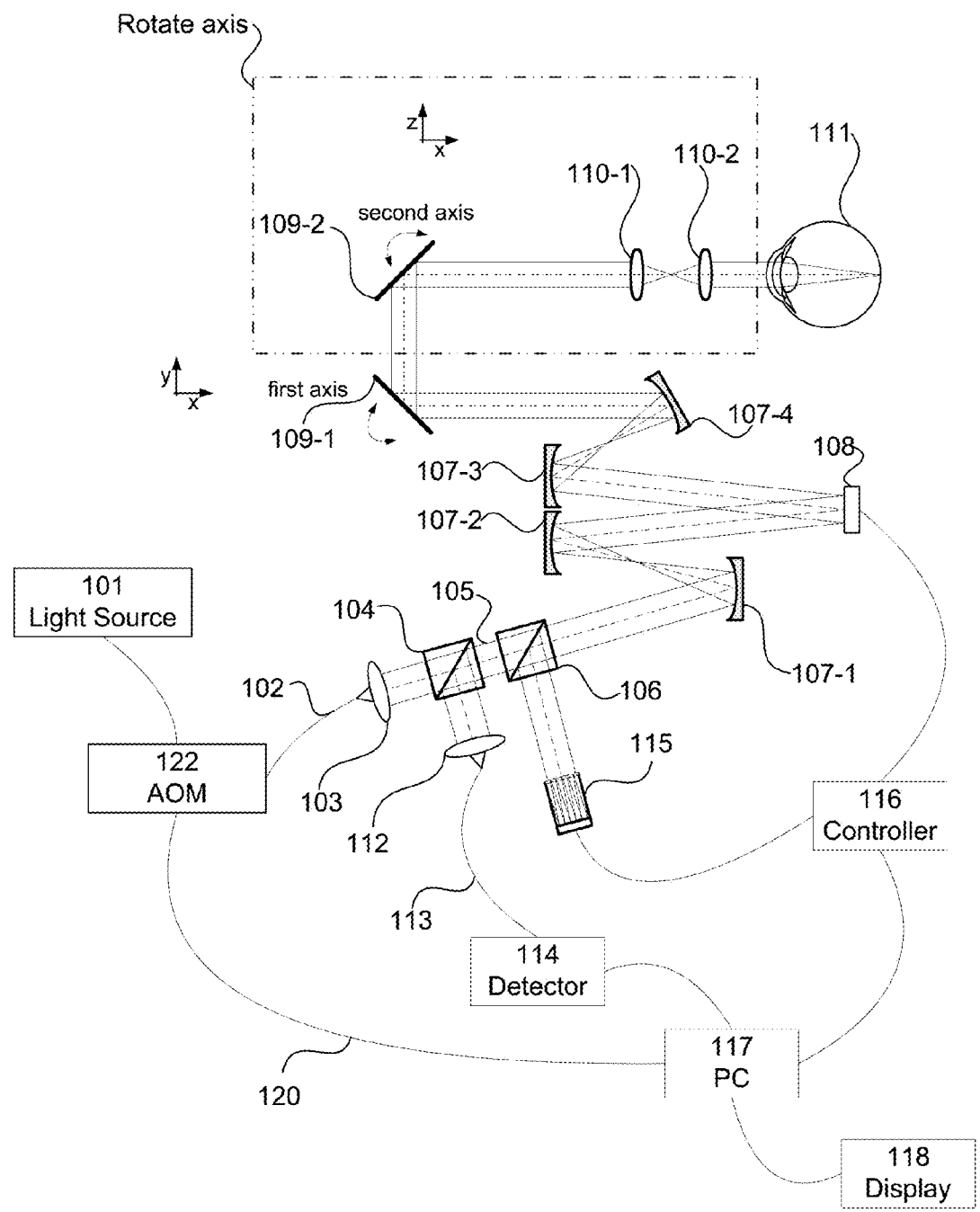
FIG. 1 is an illustration of an ophthalmoscope.

Embodiments will be described below with reference to the attached drawings. Further, an image photographing apparatus as disclosed in the following can be applied to an object to be inspected such as an eye to be inspected, skin, and internal organs.

Ophthalmoscope

A first embodiment is described with reference to of a fundus image photographing apparatus such as the photographing apparatus illustrated in FIG. 1.

Embodiments are directed towards systems, methods, and software which are used in connection with an imaging system such as an ophthalmoscope. FIG. 1 is an illustration of an exemplary ophthalmoscope. An ophthalmoscope is a system or apparatus for obtaining information about an interior portion of the eye 111 (e.g., the fundus).

An exemplary embodiment may be a scanning ophthalmoscope. A scanning ophthalmoscope scans a spot across the eye. The spot may be a spot of light from a light source that is scanned across the eye.

In an exemplary embodiment, the spot of light is produced by a light source 101. The light source 101 may be incorporated into the ophthalmoscope; alternatively, the ophthalmoscope may include an input for receiving a light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare for a person to be inspected and to maintain imaging resolution.

In one embodiment the light source is directly modulated by a modulation signal 120. In an alternative embodiment, an external modulator 122 is used to modulate the light source. The external modulator may be incorporated into the light source 101 or may be connected to the light source via an optical fiber or free space optics.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration of an exemplary embodiment, the light source 102 is polarized and single-mode optical fiber 102 is polarization maintain fiber. In another configuration of an exemplary embodiment, the polarization adjusting member may be placed after the collimator 103. Alternatively, the polarization adjusting member may be replaced with a polarizer.

The measuring light 105 radiated from the collimator 103 passes through a light division portion 104 including a beam splitter. An exemplary embodiment may include an adaptive optical system. Exemplary embodiments include both systems that do and do not include the adaptive optical system.

The adaptive optical system includes a light division portion 106, a wave front sensor 115, wave front correction device 108, and reflective mirrors 107-1 to 107-4 for guiding the measuring light 105 to those components. The reflective mirrors 107-1 to 107-4 are provided to guide the measuring light 105 to and from the pupil of an eye 111, the wave front sensor 115, and the wave front correction device 108. The wave front sensor 115 and the wave front correction 108 device may be in an optically conjugate relationship. A beam splitter may be used as the light division portion 106. The wave front sensor 115 may be a Shack-Hartmann sensor.

The measuring light 105 passing through the light division portion 106 is reflected on the reflective mirrors 107-1 and 107-2 to enter the wave front correction device 108. The measuring light 105 reflected on the wave front correction device 108 and is further reflected on the reflective mirrors 107-3 and 107-4.

In an exemplary embodiment, one or two spatial phase modulators including a liquid crystal element is used as the wave front correction device 108. The liquid crystal element may modulate a phase of only a specific polarized component. In which case, two liquid crystal elements may be employed to modulate substantially orthogonal polarized components of the measuring light 105. In an alternative embodiment, the wave front correction device 108 is a deformable mirror.

The measuring light 105 reflected off mirror 107-4 is two-dimensionally scanned by a scanning optical system 109. In an exemplary embodiment, the scanning optical system 109 includes a first scanner 109-1 and a second scanner 109-2. The first scanner 109-1 rotates around the first axis, while the second scanner 109-2 rotates around a second axis. The first axis is substantially orthogonal to the second axis.

FIG. 1 illustrates the first scanner 109-1 rotating in the x-y plane, while the second scanner 109-2 is rotating in the z-x plane. In the context of the present application, rotating the measuring light 105 in a first plane around the first axis is equivalent to rotating the measuring light 105 in the first plane and is equivalent to scanning the spot of light in the main scanning direction or the lateral direction of the object being imaged. In the context of the present application, rotating the measuring light 105 in a second plane around the second axis is equivalent to rotating the measuring light 105 in the second plane and is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single scanning mirror that is rotated around the first axis by the first scanner 109-1 and around the second axis by the second scanner 109-2 that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency.

The measuring light 105 scanned by the scanning optical system 109 is radiated to the eye 111 through eyepieces 110-1 and 110-2. The measuring light radiated to the eye 111 is reflected, scattered, or absorbed on the fundus. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Reflected light which is produced by reflection or scattering on a retina of the eye 111 then travels in the reverse direction along the same path as in the case of incident light. A part of the reflected light is reflected by the light division portion 106 to the wave front sensor 115 to be used for measuring a light beam wave front.

In an exemplary embodiment, a Shack-Hartmann sensor is used as the wave front sensor 115. However, an exemplary embodiment is not limited to a Shack-Hartmann sensor. Another wave front measurement unit, for example, a curvature sensor may be employed or a method of obtaining the wave front by reverse calculation from the formed spot images may also be employed.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a control unit 117 into an image of the object, and the image is displayed on a display 118.

The wave front sensor 115 is connected to an adaptive optics control unit 116. The received wave front is transferred to the adaptive optics control unit 116. The wave front correction device 108 is also connected to the adaptive optics control unit 116 and performs modulation as instructed by the adaptive optics control unit 116. The adaptive optics control unit 116 calculates a modulation amount (correction amount) for correction to obtain wave front having no aberration based on the wave front obtained by a measuring result of the wave front sensor 115, and instructs the wave front correction device 108 to perform the modulation according to the modulation amount. The wave front measurement and the instruction to the wave front correction device are repeated and feedback control is performed so as to obtain a suitable wave front.

In an exemplary embodiment the light division portions 104 and 106 are fused fiber couplers. In an alternative exemplary embodiment, the light division portions include partially reflective mirrors.

The detector 114 may detect reflections or fluorescence associated with the scanning spot. The detection system may make use confocal microscopy techniques in which an aperture associated with the scanning spot is used to increase the resolution and/or contrast of the detection system.

Scanner

Figure 2A:
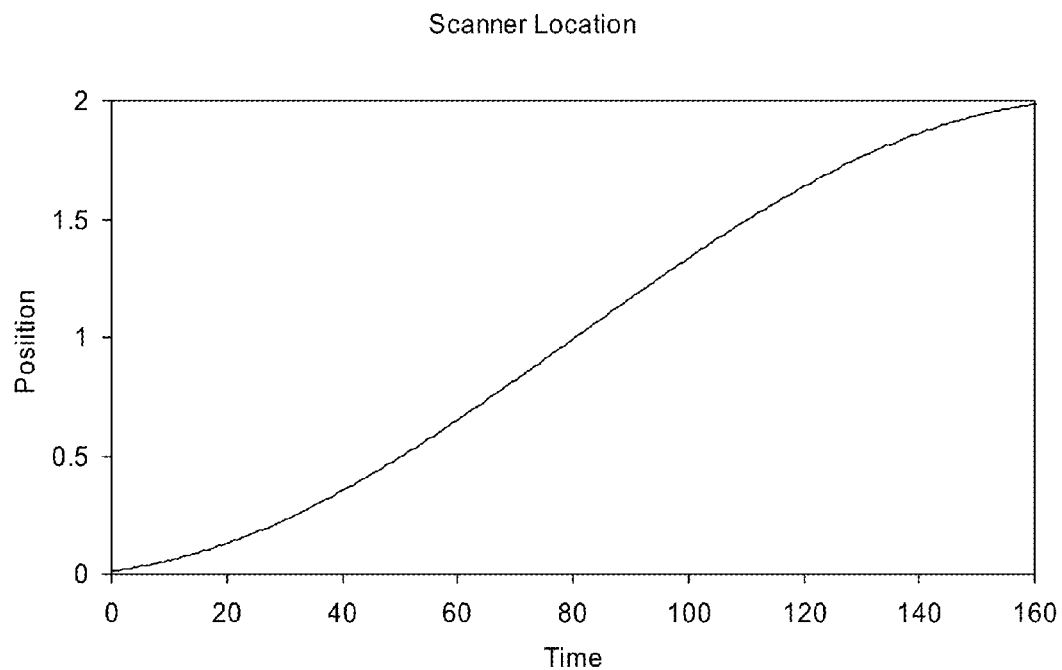
FIGS. 2A-D are illustrations of scanning position, velocity and intensity.

An exemplary embodiment is a scanning microscope such as a laser confocal microscopes or a scanning laser ophthalmoscope (SLO). The scanning microscope obtains a two dimensional image of a specimen using two scanners 109-1 and 109-2 to dynamically update positions of a laser spot on the specimen. In an exemplary embodiment the two scanners are a resonant scanner 109-1 (fast scanner) and a linear scanner 109-2 (slow scanner). The fast scanner 109-1 is driven by a sinusoidal signal to achieve high-speed scanning hence its physical motion is also sinusoidal or very close to sinusoidal. The slow scanner is usually driven by a periodic ramp signal or saw-tooth signal. The motion of the laser spot in the main scanning direction may be approximated with formula 1. In which $\omega$ is the scanning frequency, A is the scaling factor, $\phi$ is the phase offset, and f(t) is the non-sinusoidal motion. The scanning position as a function of time is illustrated in FIG. 2A.

$$x(t)=A\sin(\omega t+\phi)+f(t) \quad (1)$$

Figure 2B:
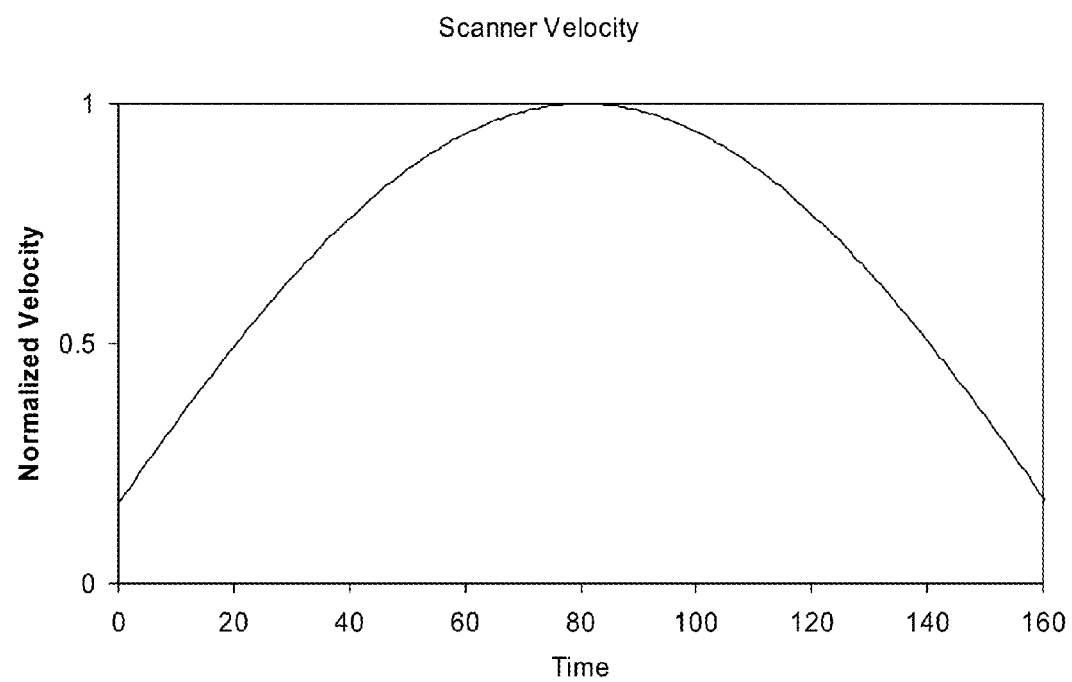
Figure 2C:
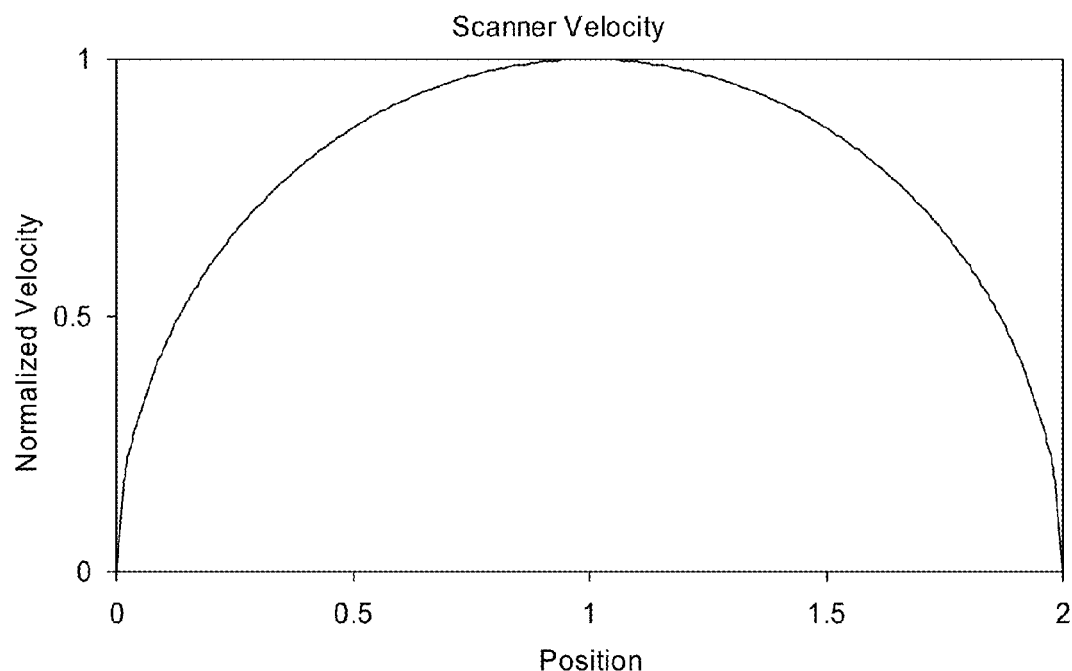

Due to the sinusoidal effect, the speed of the fast scanner 109-1 at the center of the scanning area is much faster than that at the edge of the scanning area. The speed of the laser spot in the main scanning direction may be approximated with formula 2. The scanning velocity as a function of time is illustrated in FIG. 2B. The scanning velocity as a function of scanning position is illustrated in FIG. 2C.

$$v(t)=\frac{dx(t)}{dt}=A\omega\cos(\omega t+\phi)+f'(t) \quad (2)$$

Figure 2D:
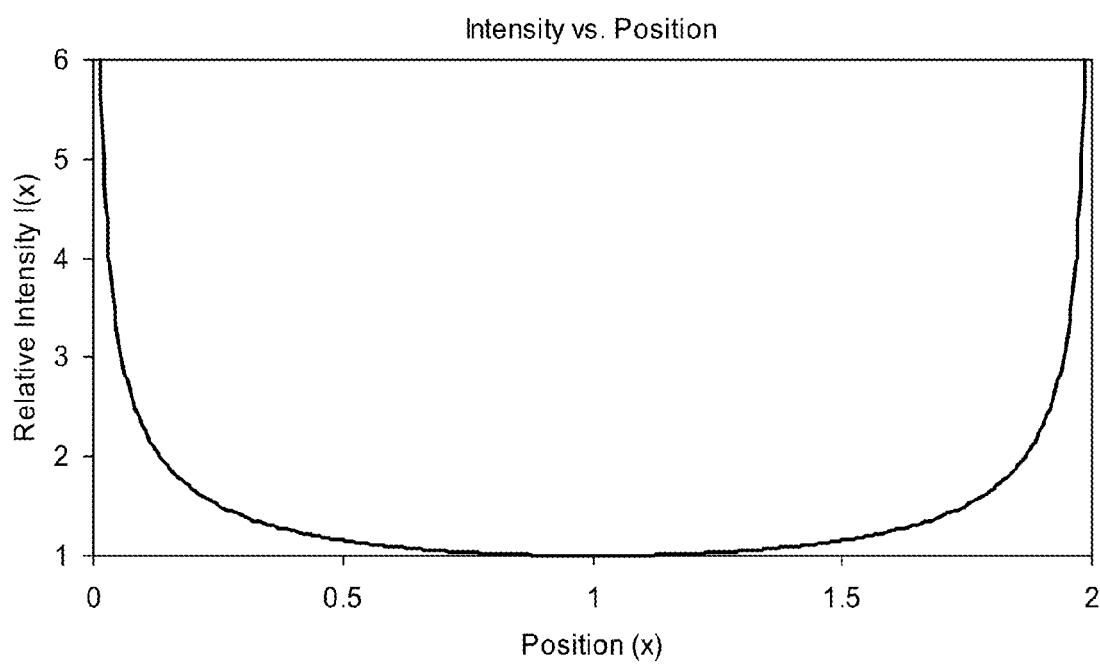

When the laser output has uniform power over time, this sinusoidal effect causes non-uniform distribution of laser energy across the fast scanning field of view (FOV), where a unit area at the two edges receives significantly more laser energy than a unit area at the center does. The inventors have found that the intensity I(t) of the laser spot as it moves in the main scanning direction is approximately inversely proportional to the velocity of the laser spot in the main scanning direction as described in formula 3. FIG. 2D is an illustration of the laser intensity of the laser spot as a function of the scanning position, i.e., the distribution of laser energy across the field of view.

$$I(t) \propto \frac{1}{v(t)} \quad (3)$$

This issue dramatically limits the use of laser power on live subjects, e.g., live human eyes. Based on ANSI safety levels, the worst case has to be considered before an experimental protocol is designed. In this particular case as shown in FIG.

2D, the edges of the specimen receive approximately 6 times the laser energy than the center. Therefore, researchers have to use a laser power that will be safe at the edges of the field of view, while unfortunately, the center only receives ⅙ of the laser energy that is received at the edges. This issue significantly reduces signal to noise ratio (SNR) of the image since the SNR is proportional to laser energy or the photon number.

Figure 3:
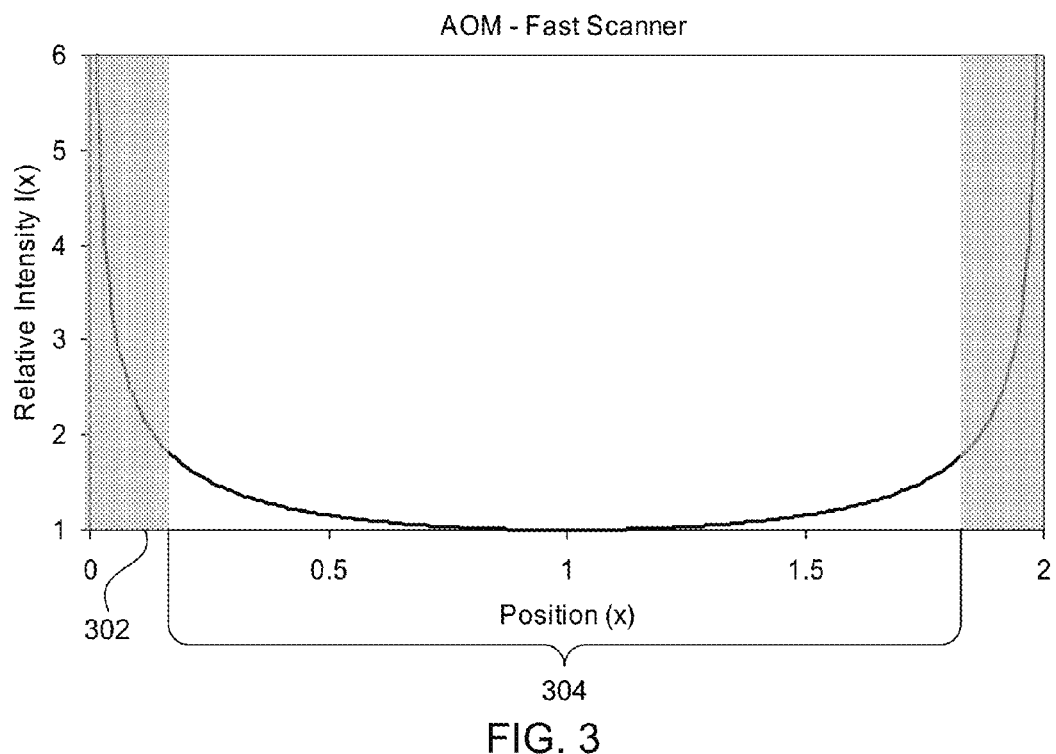
FIGS. 3-4 are illustrations of areas blocked by a modulator.

Prior art methods have employed an acoustic optical modulator (AOM) 122 to mitigate this problem by blocking laser light to the subject's eye when the fast scanner is in the slow moving area. The AOM 122 can be modulated to let light pass through only when the fast scanner is in fast moving zone. Different implementations of this prior art method allow 20%-35% of the laser light to be blocked by the AOM 122 when the resonant scanner is running in the 20%-35% slow motion zone. FIG. 3 is an illustration of this method, the shaded areas 302 are blocked by the AOM 122, while the area 304 is not blocked.

However, this prior art method does not take full advantage of the AOM 122 in that, the distribution of laser energy in the fast motion zone is still nonlinear where the new edge of the new field of view 304 receives 1.5-2 times laser energy than the center. The light is turned ON/OFF (by the AOM 122) dependent only on the motion of the fast scanner. While actually, about 5%-25% of the light is still delivered to the subject when no data (image) is sampled due to back sweeping and jitter of the slow scanner.

Figure 4:
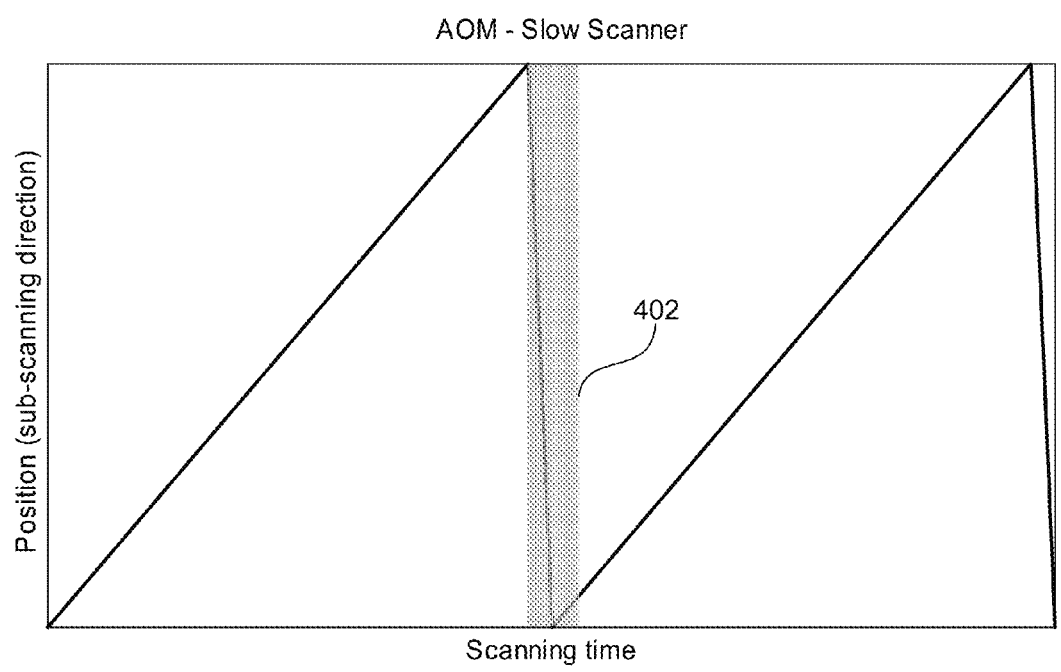

The slow scanner 109-2 is usually driven by a low frequency ramp signal, e.g., 15-60 Hz, as illustrated in FIG. 4. Data in window 402 is not usable. When the slow scanner 109-2 runs backwards the image is significantly compressed and is thus unusable. The first a few fast scanning lines of forward scanning of the slow scanner 109-2 are unusable due to jitter.

Figure 5A:
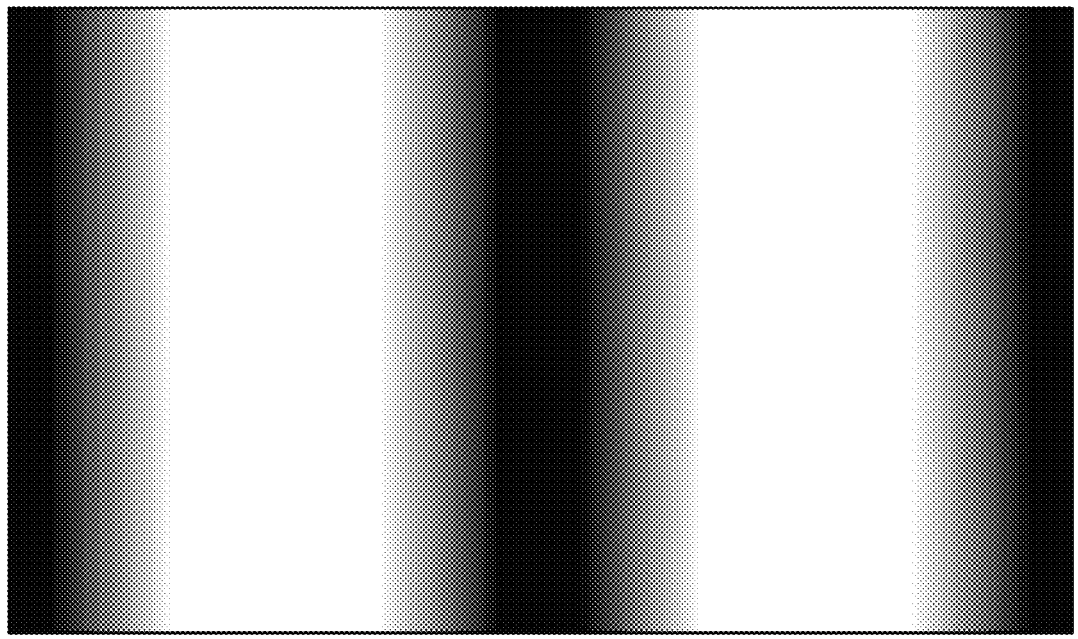
FIGS. 5A-C are illustrations of the laser intensity, and modulation windows.
Figure 5B:
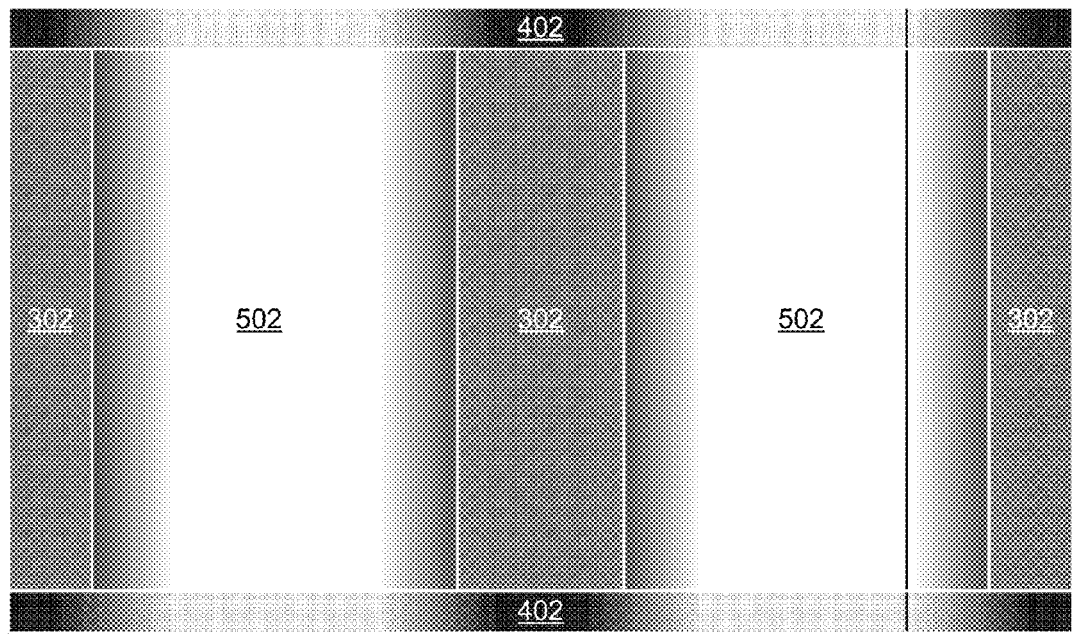
Figure 5C:
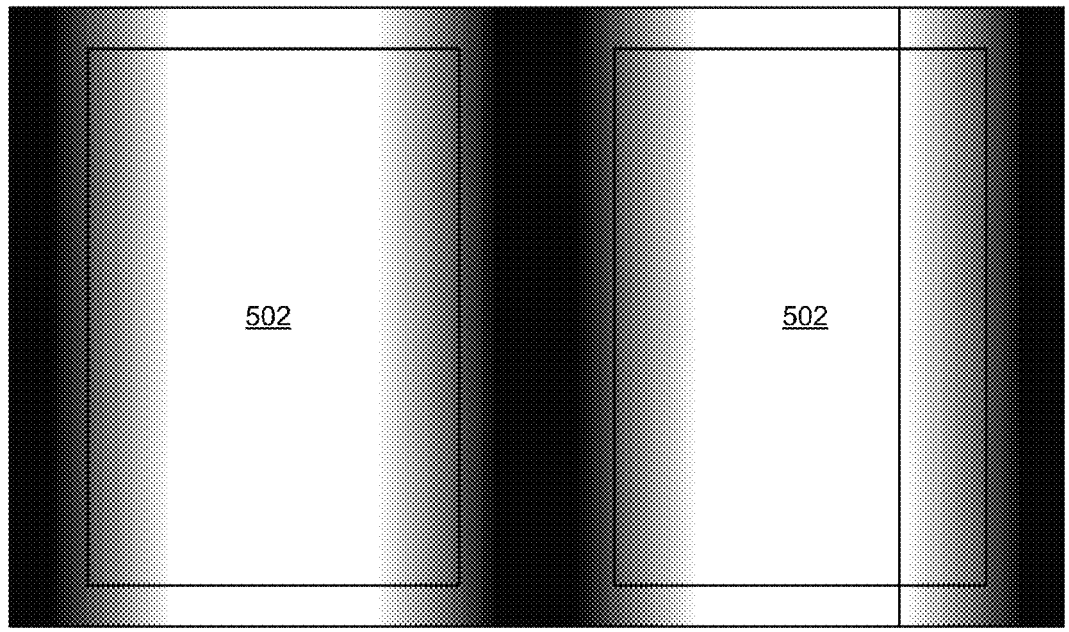

FIG. 5A is an illustration of the laser intensity experienced by a specimen in two side by side scans. The black portion shows where the laser spot intensity is the highest, and the white portion shows where the laser spot intensity is lowest. FIG. 5B is an illustration of how the AOM 122 may be used in an ON/OFF mode to block laser light during periods 302 and 402 which are shown as semi-transparent gray blocks. Data sampling windows 502 are also illustrated in FIG. 5B.

In an exemplary embodiment, a new approach is introduced to do complete laser power modulation across the two-dimensional scanning field of view. This approach allows the use of less laser power for the same SNR, or to achieve higher SNR while using the same laser power. The AOM 122 may be used to modulate the laser power. In other embodiments, other modulation tools may be used such as direct modulation, electro-optic modulation, Electro-absorption modulation.

Figure 6A:
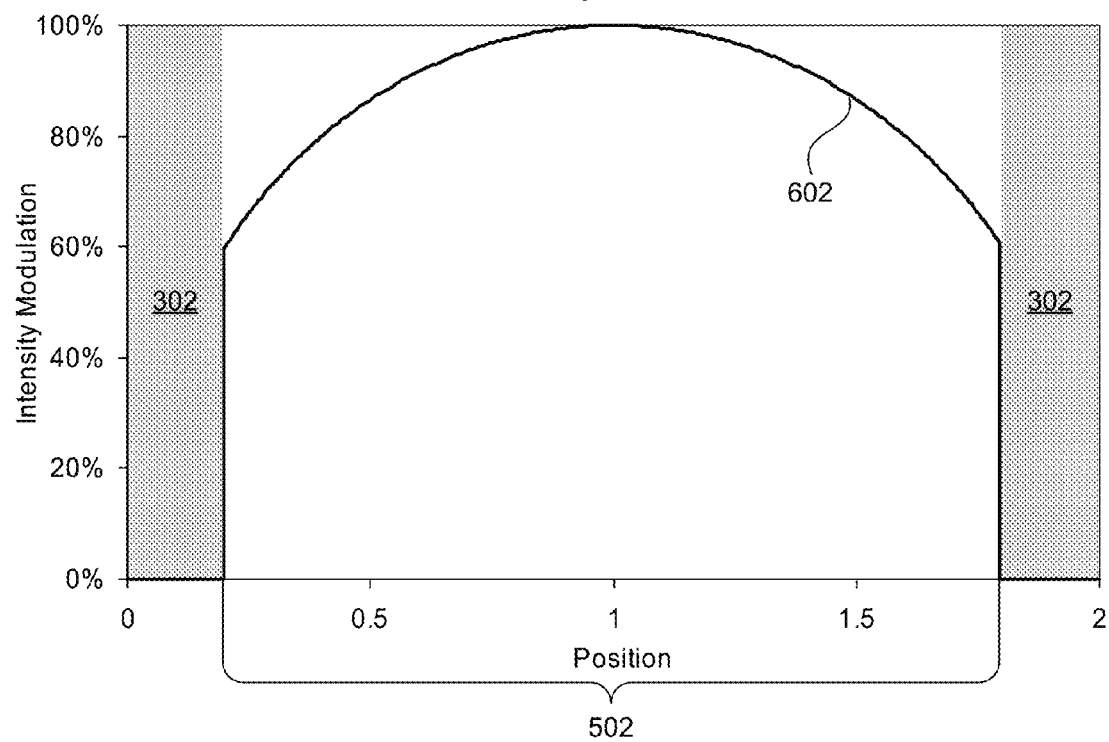
FIG. 6A is an illustration of the modulation intensity.
Figure 6B:
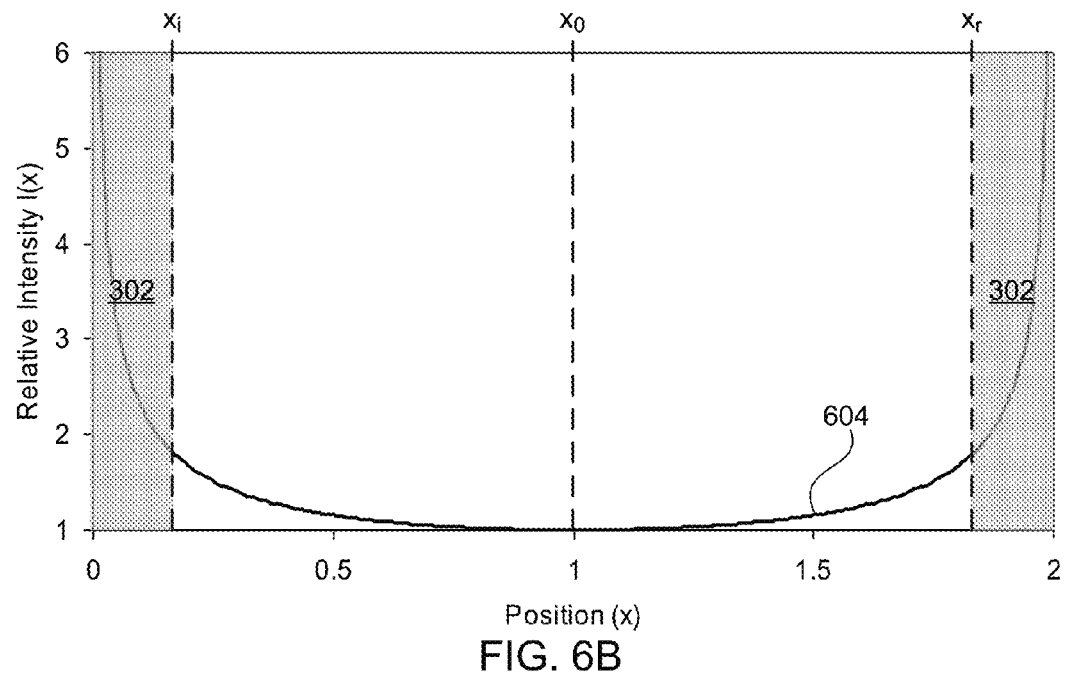
FIG. 6B is an illustration of the laser intensity and positions along the sampling window.

Inside the sampling windows 502, the laser power (i.e. the light intensity) is modulated by a nonlinear curve 604 derived from equation 3 as illustrated in FIG. 3. FIG. 6A is an illustration of the percent 602 of the laser intensity that is modulated by the AOM 122 as a function of position. With uniform laser power, the energy distribution in equation 3 as illustrated in FIG. 6B can also be written as a function of position as described in equation (4). In which $x_i$ and $x_r$ are two boundaries of the valid data sampling window 502 in the fast scanning direction as illustrated in FIG. 6B. The central location of the fast scanner $x_0$ is also illustrated in FIG. 6B.

$$I(x) = g(x) \times \epsilon [x_i, x_r] \quad (4)$$

To achieve uniform laser energy on the specimen across the fast scanning FOV 502, the laser power should be modulated in accordance with modulation pattern 602 illustrated in FIG. 6A. In an exemplary embodiment, the modulation pattern may be based on Equation 5.

$$P(x) = \frac{P(x_0)I(x_0)}{I(x)} x \in [x_i, x_r] \quad (5)$$

In equation 5, $P(x_0)$ is the laser power at the center of the fast scanning FOV, and $P(x)$ is laser power elsewhere. This means that the two edges will get less laser power and the center will get more.

In an exemplary embodiment, a Field Programming Gate Array (FPGA) with an analog-to-digital converter (ADC) and a digital-to-analog converter (DAC) can be used.

The ADC may be programmed by the FPGA to do image acquisition. The ADC receives synchronization signals (H-sync and V-sync) from the two scanners 109-1 and 109-2. The FPGA generates digitized H-sync and V-sync for DAC and other FPGA applications. The ADC can work in master mode (with an internal phase locked pixel clock) or slave mode (with an external pixel clock). This pixel clock is used as the common pixel clock for the DAC.

In an exemplary embodiment, the DAC is programmed to generate an analog signal to control the AOM, with the digitized H-sync, V-sync, and the common pixel clock from the ADC. These three clocks guarantee the DAC output is synchronized with the motion of the two scanners.

The truncated data window 502 illustrated in FIG. 5B can be achieved by adding simple offsets to the DAC signal.

In an additional exemplary embodiment, the modulation of the laser power described by equation 5 includes additional pre-correction. The motion of the fast scanner is not linear in space domain. The laser power (not energy) is sinusoidal across the fast scanning FOV, as described by equations (1)-(3).

Once the laser power modulation is applied in step 5, the raw image with sinusoidal distortion will have a bright center and dim edges across fasting scanning FOV. The reason for this is that each pixel on the raw image has equal sampling time. Brightness of a pixel is determined by equation 6.

$$E = P\Delta t \quad (6)$$

Where E is the energy, P is the power, and $\Delta t$ is the exposure time. In one exemplary embodiment, $\Delta t$ is the same for all pixels on the raw image, but P is small at the two edges and large at the center. When the energy E is used to calculate eye safety values $\Delta t$ should be considered the same for all values. When the energy E is used to calculate the amount of energy detected at the detector, $\Delta t$ may be based on the pixel clock. In one exemplary embodiment, the pixel clock is constant. In an alternative exemplary embodiment, the pixel clock varies with position.

In one embodiment the raw image is corrected for sinusoidal distortions. However, the sinusoidal correction may be done using integration or interpolation. To correct for sinusoidal distortion, in a unit area of the specimen, the edge areas need more raw pixels than the central area does.

Table 1 illustrates usage of laser power in three different mode of operation to achieve the same SNR.

TABLE 1

| Laser power to achieve the same SNR | |
|---|---|
| Without modulation as in the prior art | $P(x_O)$ |
| Simple modulation as in the prior art | 0.25~0.4 $P(x_O)$ |
| Complex modulation as disclosed herein | 0.12~0.2 $P(x_O)$ |

In general, the modulation curve is related to the velocity of the scan, as described in equation 6a.

$$M(t) = K(v(t)) \quad (6a)$$

One example of this relationship is described below. In one exemplary embodiment the modulation curve $M(t)$ is inversely proportional to the average intensity at a point being illuminated on the sample as described in equation (7) within a specific scanning window.

$$M(t) \propto \frac{1}{\langle I(t) \rangle_{\Delta t}} \propto \langle v(t) \rangle_{\Delta t} \quad (7)$$

As stated in equation (3) the intensity is inversely proportional to the velocity. The inventors have discovered that the modulation can be proportional the average velocity at the point being illuminated on the sample. Equation 8 describes how the modulation can also be written in integral form.

$$M(t) \propto \langle v(t) \rangle_{\Delta t} \propto \frac{1}{\Delta t} \int_{t-\frac{\Delta t}{2}}^{t+\frac{\Delta t}{2}} v(t) dt \quad (8)$$

Equation (2) may be used to solve the integral in equation (8) so that the modulation can also be written in terms of the position of the spot on the sample as described in equation (9).

$$M(t) \propto \frac{1}{\Delta t} \int_{t-\frac{\Delta t}{2}}^{t+\frac{\Delta t}{2}} v(t) dt \propto \frac{1}{\Delta t} x(t) \Big|_{t-\frac{\Delta t}{2}}^{t+\frac{\Delta t}{2}} \quad (9)$$

The modulation curve may also be described over the entire field of view using Equation (10).

$$M(t) \propto \frac{1}{\Delta t} x(t) \Big|_{t-\frac{\Delta t}{2}}^{t+\frac{\Delta t}{2}} x \in [x_i, x_r] = 0 \ x \notin [x_i, x_r] \quad (10)$$

In addition, the intensity of the laser is not modulated at position $x_0$. A time $t_0$ may be defined in terms of $x_0 = x(t_0)$. In which $x_0$ is the central location of the fast scanner as illustrated in FIG. 6B. So that equation 10 may be written more exactly as Equation (11).

$$M(t) = \frac{\langle v(t) \rangle_{\Delta t}}{\langle v(t_0) \rangle_{\Delta t}} \quad (11)$$

$$= \frac{x(t) \Big|_{t-\frac{\Delta t}{2}}^{t+\frac{\Delta t}{2}}}{x(t) \Big|_{t_0-\frac{\Delta t}{2}}^{t_0+\frac{\Delta t}{2}}} x \in [x_i, x_r]$$

$$0 \ x \notin [x_i, x_r]$$

An exemplary embodiment allows you to optimize the image quality even if you use non-even illumination for a laser scanning microscopy system using a resonant scanner. An exemplary embodiment will modulate laser not only at on/off status, but also intensity of the laser power. By modulating laser intensity, the laser power can be accurately modulated to a different level at different scanner locations. Spatial/temporal resolution of the modulation is limited by the pixel clock only, e.g., tens of nanoseconds or less than one micrometer, and the accuracy of the laser power is limited by the resolution of digital to analog device. An exemplary embodiment will reduce of the use of laser power to the subject at least 50% compared to the existing technologies, or the signal-to-noise ratio (SNR) of the image will be increased by at least a factor of 2 when the same laser power is used.

Figure 7:
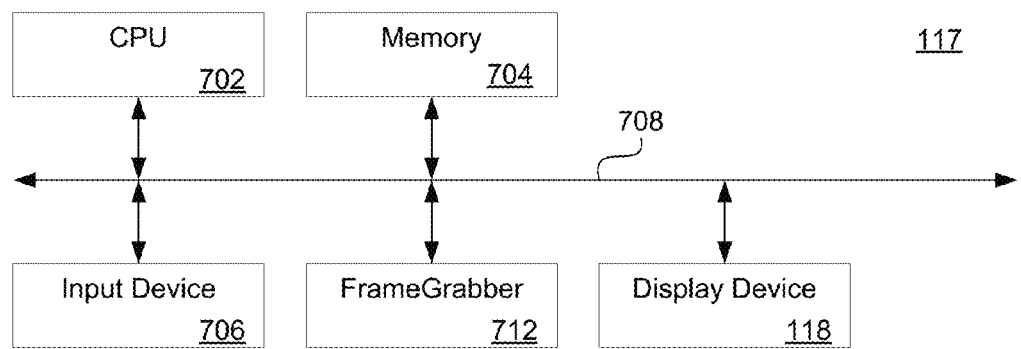
FIG. 7 is an illustration of a controller.

FIG. 7 is an illustration of a device 117 that may be used to implement an exemplary embodiment. The device 117 may be a personal computer or a custom built computing device. The device 117 includes a central processing unit (CPU) 702 for executing instructions. The instructions may be encoded on a non-transitory computer readable medium. The non-transitory computer readable medium may include a recording medium, such as a hard disk, a floppy disk, an optical disk, a magnetic disk, a magneto-optical disk, a magnetic tape, and a non-volatile memory card, and a drive for driving the recording medium and recording information in it. The instructions and the data on which the instructions are performed may be stored in a memory 704. The device may include an input device 706 such as a keyboard, a mouse, touch panel, a stylus, and/or one or more buttons which provides a user with a method for providing information to the device. A bus 708 includes an address bus or a data bus and is connected to each unit in the configuration. The device 117 may include or be connected to a display device 118. The display device 118 can be used to display the state of the device and/or various input operations and processing results. The display device 118 can be formed of an LCD (liquid crystal display), a PDP (plasma display panel), an OLED (organic light-emitting diode), or the like, and can display images and/or text. The device 117 may include or be connected to a frame grabber 712 that is connected to detector 114.

Aspects of exemplary embodiment can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of an exemplary embodiment.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An imaging system for imaging an object, comprising:
a scanner, wherein the scanner positions a spot of light from a light source on the object along a scanning path, the scanning path includes a plurality of scan lines, wherein the spot moves along the scanning path at a scanning velocity, wherein the scanning velocity is not constant;

a detector arranged to output data associated with positions along the scanning path; and one or more processors that perform calculations comprising:
- calculating pixels based on the output data; and
- constructing an image of the object based on the pixels;

wherein, intensity of the spot of light is modulated as a function of the scanning velocity during a first window, and the intensity of the spot of light is substantially zero outside of the first window.

2. The imaging system of claim 1, further comprising an external modulator for modulating the light source.

3. The imaging system of claim 1, wherein the light source is directly modulated.

4. The imaging system of claim 1, further comprising calculating the pixels by integrating the intensity of the detected light.

5. The imaging system of claim 1, wherein the intensity of the spot of light is modulated as a function of the average scanning velocity.

6. The imaging system of claim 5, wherein the average scanning velocity is averaged over a period equal to the pixel clock time.

7. The imaging system of claim 1, wherein the scanner is a resonant scanner that positions the spot of light with sinusoidal motion; and
- wherein constructing the image further comprises correcting image distortion caused by the sinusoidal motion by integration.

8. An imaging method for imaging an object, comprising:
- scanning a spot of light from a light source on the object along a scanning path, the scanning path includes a plurality of scan lines, wherein the spot moves along the scanning path at a scanning velocity, wherein the scanning velocity is not constant;
- modulating intensity of the spot of light as a function of the scanning velocity during a first window, and the intensity of the spot of light is substantially zero outside of the first window;
- detecting output data associated with positions along the scanning path;
- calculating pixels based on the output data; and
- constructing an image of the object based on the pixels.

9. A non-transitory computer readable medium encoded with instructions for imaging an object, comprising:
- sending instructions to a scanner to scan a spot of light from a light source on the object along a scanning path, the scanning path includes a plurality of scan lines, wherein the spot moves along the scanning path at a scanning velocity, wherein the scanning velocity is not constant;
- sending instructions to modulate intensity of the spot of light as a function of the scanning velocity during a first window, and the intensity of the spot of light is substantially zero outside of the first window;
- receiving output data from a detector, the output data associated with positions along the scanning path;
- calculating pixels based on the output data; and
- constructing an image of the object based on the pixels.

10. The imaging system of claim 1, wherein the first window is a data sampling window used for constructing the image.

11. The imaging system of claim 1, wherein the object is a fundus.

12. The imaging system of claim 1, wherein the intensity of the spot of light is modulated so that the intensity of the spot of light at an edge of the first window gets less laser power and the intensity of the spot of light at a center of the first window gets more laser power.

13. The imaging system of claim 1, wherein the scanner rotates around a predetermined axis.

* * * * *